United States Patent [19]

Dees et al.

[11] Patent Number: 4,599,227
[45] Date of Patent: Jul. 8, 1986

[54] INJECTABLE PHARMACEUTICAL PREPARATION FOR THE INDUCTION OF MULTIPLE FOLLICULAR GROWTH

[75] Inventors: H. Craig Dees, Oregon; Ronald D. Schultz, Verona, both of Wis.

[73] Assignee: Wisconsin Alumni Research Foundation, Madison, Wis.

[21] Appl. No.: 549,666

[22] Filed: Nov. 7, 1983

[51] Int. Cl.⁴ .......................... A61K 9/42; C07K 7/10
[52] U.S. Cl. .......................................... 424/38; 514/12
[58] Field of Search .......................... 424/177, 19, 38; 514/12

[56] References Cited

U.S. PATENT DOCUMENTS

| 4,186,183 | 1/1980 | Steck et al. | 424/19 |
| 4,192,859 | 3/1980 | Mackaness et al. | 424/5 |
| 4,217,344 | 8/1980 | Vanlerberghe et al. | 424/19 |
| 4,235,871 | 11/1980 | Papahadjopoulos et al. | 424/19 |

*Primary Examiner*—Delbert R. Phillips
*Assistant Examiner*—F. T. Moezie
*Attorney, Agent, or Firm*—David J. Houser

[57] ABSTRACT

An injectable pharmaceutical preparation for the induction of multiple follicular growth in mammals. A superovulation inducing hormone selected from the group consisting of follicle stimulating hormone and pregnant mare serum gonadotropin in aqueous solution is encapsulated within liposomes. The liposomes have the following characteristics: when encapsulating the hormone and injected into cows five days prior to estrus, the liposomes produce multiple follicular development as monitorable by rectal palpation of the ovaries.

17 Claims, No Drawings

INJECTABLE PHARMACEUTICAL PREPARATION FOR THE INDUCTION OF MULTIPLE FOLLICULAR GROWTH

TECHNICAL FIELD

The present invention relates to drug therapies for the stimulation of ovaries in female mammals to produce ova and, in particular to the induction of multiple follicular growth.

BACKGROUND OF ART

Embryo transfer is a technique whereby a fertilized egg is removed from a female mammal and introduced into the uterus of a second female, where it implants and develops in the normal way. Embryo transfer has become popular as a means for proliferating desirable genotypes, effecting the genetic improvement of food animals, increasing production of food animals, and treating infertility problems. The ova of a desirable female can be fertilized and harvested at each estrus without damage to the animal. Thus, offspring may be procured without the interruption of the production of such ova that would otherwise result from pregnancy in the donor animal.

It is also possible and especially desirable to stimulate the production of several ova at each estrus, effectively multiplying the reproductive capacity of the animal. The induction of multiple follicular growth with subsequent ovulation is referred to as "superovulation." For example, it is an established commercial practice to stimulate the formation of multiple ovarian follicles in cattle by multiple injections of follicle stimulating hormone. Follicle stimulating hormone is prepared from the pituitary glands of slaughtered animals and is a conventional and commercially available material. It is not necessary to use follicle stimulating hormone prepared from specifically bovine pituitary glands in order to stimulate multiple follicular growth in cows. Instead, hormone from pigs, cattle, horses, and the like can be used interchangeably with practical success. Consequently, in the commercial production of follicle stimulating hormone for use with farm animals, no attempt is made to separate such material by species.

Follicle stimulating hormone is a material prepared with attention to its practical effect rather than its purity of precise content. Thus, it would probably be possible to separate out and define a component of commercial follicle stimulating hormone that in fact is responsible for its biological activity. Herein, "follicle stimulating hormone" shall be taken when appropriate to encompass both the commercial preparation and whatever component thereof may be found to be its biologically active ingredient. References to specific amounts shall be to the commercial preparation.

A typical regimen of follicle stimulating hormone treatment in cattle includes a five-day course of injections of the hormone given intramuscularly twice a day to the donor animal just prior to natural or induced estrus. A typical total dose of the hormone is approximately 50 mg divided into ten doses. The largest dose of follicle stimulating hormone is given early, with daily doses decreasing in amount until the total of 50 mg has been given. Other conventional regimens requiring ten innoculations over a five-day period require as much as 73 mg of hormone. See James F. Evans, "Embryo Transfer in Cattle," *Large Animal Supplement,* Continuing Education Article #8, Vol. II, No. 6 (June, 1980), publ. by Compendium of Continuing Education, p. 591. Thus, it is common for the induction of superovulation to involve ten innoculations over a period of five days of follicle stimulating hormone alone. As a consequence simply of experiencing the needle so often over so short a period, the cow may become cranky, difficult to work with, and even dangerous. In addition, considerable veterinary or technician time is required. Furthermore, the typical minimum dose of approximately 50 mg of follicle stimulating hormone represents a considerable financial investment, as the hormone is an expensive material, in addition to the cost of the veterinary time needed to administer it in multiple injections.

Various attempts have been made to reduce the numbers of injections of follicle stimulating hormone necessary to produce a desirable amount of superovulation. See, for example, C. R. Looney, et al., "Comparison of Follicle Stimulating Hormone (FSH) in Gelatin and Saline Diluents for Superovulating Donor Cattle, " *Theriogenology,* Vol. 17, No. 1, (January 1982) p. 97. However, follicle stimulating hormone appears to have a relatively short half life in blood serum, making the repeated injections necessary to maintain desirable serum levels over an extended period. Attempts also have been made to avoid repeated injections by incorporating the hormone in various vehicles adapted to release the hormone more slowly into the bloodstream. However, these attempts have not been very successful, as is reported by David A. Morrow, *Current Therapy in Theriogenology: Diagnosis, Treatment and Prevention of Reproductive Diseases in Animals,* (W. B. Saunders Company: 1980) p. 75. As a consequence, large amounts of follicle stimulating hormone and the multiple injection technique have remained necessary.

Liposomes have been used for entrapment of various materials, including drugs. See for example, Michael W. Fountain, Craig Dees, and Ronald D. Schultz, "Enhanced Intracellular Killing of *Staphylococcus aureus* by Canine Monocytes Treated with Liposomes Containing Amicacin, Gentamicin, Kanamycin, and Tobramycin," *Current Microbiology,* Vol. 6 (1981), pp. 373–376. It has not been known to encapsulate follicle stimulating hormones in liposomes in injectable form for time-delayed release of the hormone in cattle.

BRIEF SUMMARY OF THE INVENTION

The present invention is summarized in that an injectable pharmaceutical preparation for the induction of multiple follicular growth in mammals includes superovulation inducing hormone entrapped within liposomes adapted to release over a selected period of time a continually pharmaceutically effective amount of the superovulation inducing hormone into the tissue of a mammal injected with the preparation.

A primary object of the invention is to provide a means for maintaining a pharmaceutically active level of superovulation inducing hormone in the blood serum of a female mammal in order to induce multiple follicular growth.

A second object of the invention is to provide means for so maintaining a pharmaceutically active level of superovulation inducing hormone such that a single injection will be sufficient over a period of as much as five days.

Another object of the invention is to provide means for maintaining such a pharmaceutically active amount of superovulation inducing hormone in the bloodstream of a mammal with the use of reduced total amounts of the hormone.

Other object, features, and advantages of the invention will be apparent from the following detailed description of a preferred embodiment of the invention.

DETAILED DESCRIPTION OF THE PREFERRED EMBODIMENT

In general terms, the pharmaceutical preparation of the invention includes a combination of a solution of superovulation inducing hormone in normal saline and preferably multilamellar liposomes with superovulation inducing hormone entrapped between the liposome membranes. For convenience of description, follicle stimulating hormone, as described and defined above, shall be taken as a typical superovulation inducing hormone, and the description of the preferred embodiment shall be made generally with reference to follicle stimulating hormone. However, other superovulation inducing hormones, such as pregnate mare serum gonadotropin, are known and may be substituted functionally for follicle stimulating hormone in a manner known to those skilled in the art.

A liposome must be selected that exhibits a desired degree of stability when injected preferably intramuscularly, into the donor animal. The preferred liposome for use in cattle is formed from a mixture of egg phosphatidylcholine and stearylamine, as is described in Example 1, below. However, liposomes formed from egg phosphatidylcholine, stearylamine, cholesterol (as described in Example 2, below) have also proved effective, although not ideal for the pharmaceutical preparation of the invention.

Liposome formation as such is a known process. A lipid is dissolved in an appropriate solvent, chloroform and methanol in a 2:1 ratio by volume being that preferred for the purposes of the invention. Then, the solvent is removed by evaporation, whereupon a lipid film is formed on the inside surface of a flask or other container in which the dissolved lipid has been held. When the lipid film is again immersed in saline, it ruptures and folds in upon itself, forming envelopes and capsules commonly referred to as liposomes. In this process, some of the saline solution and any material dissolved in it is trapped between lipid layers. Multilamellar liposomes are formed as a consequence of such immersion in saline accompanied by physical agitation for several minutes. Multilamellar liposomes can be subdivided and broken up into unilamellar liposomes by sonication. Multilamellar liposomes are the larger of the two but are still small enough to be injected intramuscularly.

Egg phosphatidylcholine is inexpensie and available and therefore is the lipid preferred for the making of the pharmaceutical preparation of the invention. However, phosphatidylcholine from other sources is equally efficacious and shall be understood to be included in the term "egg phosphatidylcholine" whenever used herein. Various other materials may be incorporated in the lipid film by dissolving them, together with the lipid, before evaporation. The presence of stearylamine in the lipid film leads to an increased space between liposome membranes in multilamellar liposomes, apparently because of electrostatic repulsion. Cholesterol incorporated in liposome membranes tends to make them more stable and resistive to degeneration.

To procure the pharmaceutical preparation of the invention, liposome films having varying proportions of egg phosphatidylcholine, stearylamine, and cholesterol were formed and were utilized to make liposomes in which follicle stimulating hormone was entrapped. As is set forth below, liposomes prepared from a combination of egg phosphatidylcholine and stearylamine in a 7:1 molar ratio proved most desirable for the purposes of the invention. However, egg phosphatidylcholine, cholesterol, and stearylamine in a 7:2:1 molar ratio also proved effective though less preferred in making the pharmaceutical preparation of the invention.

It was verified that follicle stimulating hormone had indeed been entrapped within the liposomes rather than simply being physically associated with their surfaces. This was done by marking the follicle stimulating hormone by mixture with a selected quantity of human follicle stimulating hormone marked with $^{125}$I. As has been mentioned above, follicle stimulating hormone tends to be effective across species, the commercial preparation of follicle stimulating hormone referred to herein itself probably containing material from more than one specie. After liposomes had been made in a saline solution containing the dissolved follicle stimulating hormones so marked, the liposomes were removed from the solution by centrifuge. The supernatent containing the follicle stimulating hormones that had not been entrapped was removed and discarded. The pellet of liposomes was resuspended in normal saline, and the process was repeated to wash the surfaces of the liposomes. In other samples, the free follicle stimulating hormones, including that marked with $^{125}$I were removed from the liposomes by gel filtration chromatography using conventional procedures described by Sessa, G. et al. "Interaction of a Lytic Polypeptide, Mellitin, with Lipid Membrane Systems," *J. Biol. Chem.*, vol. 244, pp. 3575–3582 (1969).

Entrapment of follicle stimulating hormone in the liposomes was estimated quantitatively by the entrapment of the radio-labeled human follicle stimulating hormone. Actual entrapment or "true latency" was determined using conventional techniques comparable to those described by Anderson, P. et al. "Entrapment of Human Leukocyte Interferon in the Aqueous Interstices of Liposomes," *Infect. Immun.*, Vol. 31, pp. 1099–1103 (1981). By these means it was determined that approximately 18 to 19% of the follicle stimulating hormone that had been dissolved in the saline solution used to form the liposomes had been entrapped behind liposome membranes. Hormone in solution not entrapped within liposomes shall be referred to herein as "free" hormone.

It is believed that in vivo the liposomes degenerate over time, releasing the entrapped follicle stimulating hormone into the bloodstream of the injected animal. By this means, serum levels of the hormone can be kept at a pharmaceutically effective level without repeated injection. Clearly it would be possible to inject washed liposomes in isolation and achieve this effect. However, it is common to initiate a regimen of treatment with follicle stimulating hormone with a fairly large dose of the hormone. Thus, the preferred embodiment of the pharmaceutical preparation of the invention is a mixture of liposomes with entrapped follicle stimulating hormone and a solution containing free follicle stimulating hormone. Such preparation most conveniently is the very saline solution in which the liposomes have been formed. Thus, without waste or the need to employ laborious separation techniques, a single solution may be prepared in which approximately 18 to 19% of the follicle stimulating hormone is entrapped without liposomes and the remaining hormone is available for an immediate, initial dose of hormone to begin the superovulating regimen.

The kit of the invention is adapted to make the pharmaceutical preparation referred to above available for use over an extended period of time without the need to provide refrigerated storage. Futhermore, the kit is adapted to be convenient for a practitioner's use in the field, allowing him to obtain a fresh dose of the pharmaceutical preparation for immediate use with a minimum of manipulation and handling difficulties.

The kit of the the invention includes a dry container in which has been placed a selected quantity of lyophilized follicle stimulating hormone, a dry container containing dry lipid material of the sort referred to above, and a container containing a diluent of normal saline (0.85% NaCl by weight). The contents of each container are sterile. The follicle stimulating hormone and lipid containers may be separate or may be one and the same container. In either case, the container of normal saline may be a syringe also suitable for measuring and injecting the pharmaceutical preparation into the donor animal. In any event, any or all of the containers of the kit may be equipped with conventional needle puncturable elastomer plugs, so that fluid materials may be transferred from container to container via a needle-equipped syringe. Alternatively the follicle stimulating hormone and normal saline may be contained in separate containers with separate means for introducing the saline to the hormone. Such a syringe as that referred to above may then be the dry container of lipid material.

The preparation of a uniform lipid film in a flask or vial is described in Example 1, below. This is the preferred method of obtaining a dry container containing lipid material. However, lipid material in lyophilized or otherwise dried powder form is a widely available commercial material. If such a dried preparation is used, the desired amount may simply be measured into a selected dry container. In the event the dry container is a syringe, the syringe may be lipid coated in the same manner as a flask or vial. Alternatively, dry lipid material may be measured into the syringe with the needle-holding end thereof stopped in any suitable manner.

In use, the lyophilized follicle stimulating hormone is rehydrated in the normal saline solution. This may be accomplished by any conventional means of transferring materials from one container to another, including the use of a syringe. The rehydrated follicle stimulating hormone is then added to the dry lipid material, again by any conventional means, and multilamellar liposomes are allowed to form. The liposomes entrap part of the follicle stimulating hormone together with the saline in which it is dissolved, and the pharmaceutical preparation of the invention is thus produced.

When separate dry containers are employed for the follicle stimulating hormone and the lipid material, the follicle stimulating hormone rehydrated first and is then transferred to the container of dry lipid material. In the alternative embodiment disclosed above in which both the dry follicle stimulating hormone and lipid material are stored within a common container, the rehydrating of the follicle stimulating hormone and the formation of liposomes occurs simultaneously as the saline solution is added to their container. In the event the lipid container is itself a syringe, rehydrated follicle stimulating hormone is simply drawn into the syringe, where liposome formation takes place. In each case, it is desirable to agitate the solution for 10 to 15 minutes at the point that liposome formation is taking place. All of the operations referred to above may be undertaken at room temperature.

Although all of the alternative embodiments referred to above are included within the scope and spirit of the invention, it is clear that each embodiment offers particular advantages. For example, in the embodiments in which a syringe serves as a container of lipid material or saline, no separate syringe need be provided for injection of the pharmaceutical preparation in the donor animal. In the event a syringe serves as the container for the saline solution, no separate means need be provided to transfer saline to the container or containers holding the dry materials. When the follicle stimulating hormone and dry lipid material are held in a single container, the entire kit can consist of one container holding the dry ingredients and the saline-filled syringe, with no separate syringe being necessary for innoculation of the animal.

The method of the invention for inducing multiple follicular growth in a female mammal includes the injection of the pharmaceutical preparation of the invention in a single injection. The injection preferably is intramuscular and is given approximately five days before natural or induced estrus. The induction of estrus by the conventional use of pregnant mare serum gonadotropin and prostaglandin is described in James F. Evans, "Embryo Transfer in Cattle," referred to above, and materials and methods other than those described by Evans are known. The injection utilized in the method of the invention is preferably of the pharmaceutical preparation prepared from egg phosphatidylcholine and stearylamine, in a 7:1 molar ratio, referred to above. The amount of the preparation injected in the Example 4 disclosed below was that calculated to be sufficient to contain approximately 50 mg. of follicle stimulating hormone, partly in free solution and partly entrapped within liposomes. This single injection is sufficient to induce superovulation and the production of an increased number of ova, as is shown by the experimental results set forth in Example 4, below. Ideal dosage may be expected to vary with the type and size of cow. The ideal dosage may be easily determined by one skilled in the art by a series of trials on typical cows.

The following are specific examples setting forth the preferred method of making the pharmaceutical preparation and kit of the invention and showing experimental results relevant to application of the method of the invention, disclosed above:

EXAMPLE 1

First Example of the Pharmaceutical Preparation of the Invention 200 mg of a mixture of egg phosphatidylcholine and stearylamine in a 8:1 molar ratio were dissolved in a solvent containing chloroform and methanol in a 2:1 ratio by volume. The solution was added to a round-bottom flask. The solvent was then removed by rotoevaporation conducted at 37° C. The egg phosphatidylcholine and stearylamine were found to have formed a substantially uniform lipid film on the inside surface of the flask.

An entirely comparable solution of egg phosphatidylcholine and stearylamine was prepared and placed in a small vial. The vial was incubated at 37° C. in a water bath, and a gentle stream of sterile, dry nitrogen gas was passed over the solution. As a consequence, the solvent was removed by evaporation, and a thin lipid film remained in the vial.

Follicle stimulating hormone was procured as a freeze-dried protein powder under the trade name "FSH-P" from Burns-Biotech Co. of Omaha, Neb. 50 mg. of the follicle stimulating hormone was rehydrated in 2.5 ml of sterile, normal saline having a concentration of 0.85% sodium chloride by weight. To accomplish rehydration, the follicle stimulating hormone was simply mixed with the saline and gently agitated by hand for a brief period of time. Comparable samples of follicle stimulating hormone so hydrated were then added to each of the vial and flask referred to above containing a dry lipid film. The vial and flask were agitated for from 10 to 15 minutes at room temperature (approximately 22° C.) to assure maximal entrapment of follicle stimulating hormone and the formation of liposomes. When the liposomes are washed so as to remove from them any entrapped follicle stimulating hormone, subsequent disruption of the liposome to release entrapped follicle stimulating hormone coupled with subsequent measurement of the follicle stimulating hormone thus released indicated that approximately 18 to 20% of the follicle stimulating hormone had been entrapped. The preferred pharmaceutical preparation of the invention includes both the entrapped follicle stimulating hormone and the remaining hormone still in solution in the free saline.

Unilamellar liposomes were formed from a sample of the multilamellar liposomes produced in accord with the method just disclosed by conventional sonication of the multilamellar liposomes while they were still suspended in the saline solution in which they had formed. Sonication for from 5 to 10 minutes was found to be sufficient to produce small unilamellar liposomes.

EXAMPLE 2

Second Preparation of the Pharmaceutical Preparation of the Invention

A saline solution of follicle stimulating hormone containing multilameller liposomes having entrapped follicle stimulating hormone was prepared following substantially the same steps as those set forth in Example 1 except that the 7:1 molar ratio of egg phosphatidylcholine and stearylamine was replaced with a 7:2:1 molar ratio of egg phosphatidylcholine, cholesterol, and stearylamine. Unilamellar liposomes also were formed from a sample of this material in the manner set forth in Example 1.

EXAMPLE 3

Third Preparation of the Pharmaceutical Preparation of the Invention (Hypothetical)

From the disclosure set forth herein, one skilled in the art could prepare a saline solution of pregnant mare serum gonadotropin containing multilameller liposomes having entrapped pregnant mare serum gonadotropin by following substantially the same steps as those set forth in Examples 1 and 2.

EXAMPLE 4

Stimulation of Multiple Follicular Growth in Cattle

Cows were injected with a single dose, one injection per cow, of either multilamellar or unilamellar pharmaceutical preparations made in accord with the steps set forth in either Example 1 or 2. Injections were made both sub-cutaneously and intramuscularly. The injections were made five days before conventionally induced estrus. The ovaries of the cows were examined by rectal palpation for the induction of multiple ovarian follicles. The number of corpus lutea produced after follicle formation was determined subsequently in the same manner to ascertain the number of the induced follicles that had actually released ova. Normal unstimulated follicle formation in a cow results in one follicle and one released ova per estrus. Thus, numbers in excess of one are evidence of stimulation. The results are given below in Table 1. Liposomes formed from egg phosphatidylcholine and stearylamine are designated "PC/ST." Liposomes also containing cholesterol in the manner of Example 2 are designated PC/CHOL/ST. In each case, the single injection contained a total of approximately 50 mg of follicle stimulating hormone distributed between hormone dissolved in free saline and hormone entrapped within liposomes.

TABLE 1

| Treatment | Cow Number | Number of New Follicles | Number of Ovulated Follicles (by number of corpus lutae) |
|---|---|---|---|
| PC/ST, unilamellar, subcutaneous injection | 57 | 8–12 | 1 |
|  | 42 | 7 | 3 |
| PC/CHOL/ST, unilamellar, intramuscular injection | 228 | 4 | 3 |
|  | 230 | 3 | 1 |
| PC/ST, multilamellar, subcutaneous injection | 224 | 7 | 1 |
|  | 65 | 4 | 4 |
| PC/CHOL/ST, multilamellar, subcutaneous injection | 225 | 4 | 2 |
|  | 258 | 4 | 1 |
| PC/ST, multilamellar, intramuscular injection | 243 | 3 | 3 |
|  | 220 | 9 | 7 |
| PC/CHOL/ST, multilamellar, intramuscular injection | 50 | 2 | 0 |
|  | 237 | 2 | 0 |

Table 1 shows that a variety of liposome entrapped follicle stimulating hormone preparations made in accord with the disclosure set forth above can successfully be used to induce the formation of multiple ovarian follicles in cows after one injection. This is to be compared to the conventional procedure of inducing multiple ovarian follicles by the injection of cows twice a day for five days with follicle stimulating hormone that is not entrapped in liposomes. The most effective liposome preparation was a multilamellar preparation including liposomes prepared from PC/ST mixtures given by intramuscular injection. The other liposome preparations injected by the routes indicated successfully induced multiple follicular growth but were less efficient when compared to the preferred preparation.

Examination of three additional cows injected intramuscularly with a PC/ST preparation prepared in the manner of Example 1 but with a total of 400 ml of the 7:1 molar ratio egg phosphatidylcholine and stearylamine mixture substituted for the 200 mg used in Example 1 yielded the following results:

TABLE 2

| Treatment | Cow Number | Number of New Follicles | Number of Ovulated Follicles (by number of corpus lutae) |
|---|---|---|---|
| PC/ST, (400 mg lipid) intramuscular injection | 229 | 3 | 1 |
| | 52 | 9 | 4 |
| | 9 | 3 | 3 |

Cow numbers 9 and 52 were found to have enlarged ovaries approximately the size of tennis balls, indicated an overdose of follicle stimulating hormone that had caused the ovaries to become cystic. The amount of hormone contained in the dose given was approximately 50 mg, a typical amount given in conventional procedures in which animals are inoculated twice a day for five days. Thus, the results of Table 2 show that the amount of follicle stimulating hormone may be reduced from 50 mg to a smaller dose readily determinable with regard to animals of any given size by one skilled in the art. By this means both the total amount of injections and the total dose of costly follicle stimulating hormone can be reduced when the hormone is entrapped in a liposomal delivery vehicle.

From the experimental results set forth in this Example, one skilled in the art could determine an effective dose of the pharmaceutical preparation of hypothetical Example 3 for inducing superovulation in cattle in a like manner.

The examples and experiments set forth above show that superovulation inducing hormones can be successfully entrapped within liposomes to form a pharmaceutical preparation that releases superovulation inducing hormone into the bloodstream of an innoculated animal over a period of time. The examples of successful use with cows allow one skilled in the art to predict comparable activity in other mammals, including humans. This may have specific, advantageous effects in certain cases. For example, the use of follicle stimulating hormone or pregnant mare serum gonadotropin to induce superovulation in Rhesus monkeys is known. However, the process is successful in monkeys only once. It is thought that monkeys make an antibody upon exposure to such hormones, the antibody inactivating hormones subsequently injected to produce succeeding superovulations.

The proteolytic enzyme trypsin is known to inactivate follicle stimulating hormone. To test the ability of the liposome membranes of the pharmaceutical preparation of the invention to withstand attacks generally comparable to that to be experienced in blood serum, liposomes with entrapped follicle stimulating hormone were treated with trypsin in conventional procedures comparable to those set forth in Anderson, P. et al, "Entrapment of Human Leukocyte Interferon in the Aqueous Interstices of Liposomes," referred to above. Thereafter, the treated liposomes were again washed and tested for the presence of entrapped follicle stimulating hormone. As before, the follicle stimulating hormone had been labeled by addition of radio-labeled human follicle stimulating hormone. The activity of the radio-labeled human follicle stimulating hormone was found to have been substantially undiminshed by the trypsin treatment, indicating that the liposome membranes successfully resisted trypsin.

From the information set forth above, it may be perceived that the pharmaceutical preparation of the invention would provide means for effectively dosing animals such as monkeys that have made an antibody to follicle stimulating hormone, the lipid membrane being shown to be sufficiently resistent to enzymes comparable in disruptive force to those to be encountered in blood serum. With the liposome membrane in place, antibodies in the bloodstream of the animal would be effectively isolated from the follicle stimulating hormone until such time as the liposome finally did open to release its contents. Thus, the need for repeated injections to replenish follicle stimulating hormone in the bloodstream of the animal could be avoided in spite of the presence of antibodies to the hormone.

It is to be understood that the examples given above record only particular instances and examples of the making of the pharmaceutical preparation of the invention and of the application of the method of the invention. The present invention is not limited to the particular reagents, steps, or methods disclosed herein. Instead, it embraces all such modified forms thereof as come within the scope of the following claims.

What is claimed is:

1. An injectable pharmaceutical preparation for the induction of multiple follicular growth in mammals comprising an effective amount of a superovulation inducing hormone selected form the group consisting of follicle stimulating hormone and pregnant mare serum gonadotropin, the hormone being in aqueous solution which is encapsulated within liposomes having the following characteristics: when encapsulating the hormone and injected into cows five days prior to estrus, the liposomes produce multiple follicular development as monitorable by rectal palpation of the ovaries.

2. The pharmaceutical preparation of claim 1 wherein the liposomes include phosphatidylcholine and stearylamine.

3. The pharmaceutical preparation of claim 2 wherein the pharmaceutical preparation is adapted for the induction of multiple follicular growth in cattle, the molar ratio of phosphatidylcholine to stearylamine is 7:1, and the liposomes have the characteristic of releasing the superovulation inducing hormone in pharmaceutically effective amounts over a period of at least approximately five days, a single injection of the pharmaceutical preparation being effective to maintain the amounts.

4. The pharmaceutical preparation of claim 1 wherein the liposomes include phosphatidylcholine, cholesterol, and stearylamine.

5. The pharmaceutical preparation of claim 4 wherein the phosphatidylcholine, cholesterol, and stearylamine are in an approximate molar ratio to each other of 7:2:1 and the liposomes have the characteristic upon injection into cattle of releasing a continually pharmaceutically effective amount of superovulation inducing hormone over a period of at least approximately five days.

6. The pharmaceutical preparation of claim 1 wherein the liposomes are suspended in a normal saline solution also containing free superovulation inducing hormone.

7. The pharmaceutical preparation of claim 6 wherein the liposomes include phosphatidylcholine and stearylamine.

8. The pharmaceutical preparation of claim 7
wherein the phosphatidylcholine and stearylamine are in a molar ratio to each other of 7:1, and
the liposomes have the characteristic of releasing a continually pharmaceutically effective amount of superovulation inducing hormone released over a period of approximately five days, by means of a single injection, whereupon an initial dose of free superovulation inducing hormone is immediately available upon injection without the need for release thereof from liposomes and multiple follicular growth may be induced in cattle.

9. The pharmaceutical preparation of claim 8 wherein the liposomes include phosphatidylcholine, cholesterol, and stearylamine.

10. The pharmaceutical preparation of claim 9 wherein the molar ratio of phosphatidylcholine, cholesterol, and stearylamine to each other is approximately 7:2:1.

11. The pharmaceutical preparation of claim 8 wherein the free superovulation inducing hormone includes approximately 75 to 85% of the superovulation inducing hormone contained in the pharmaceutical preparation, the remainder being entrapped in liposomes.

12. The pharmaceutical preparation of claim 11 wherein the liposomes include phosphatidylcholine and stearylamine.

13. The pharmaceutical preparation of claim 12 wherein the phosphatidylcholine and stearylamine are in molar ratio to each other of 7:1 and wherein, upon being injected into cattle, the liposomes have the characteristic of releasing superovulation inducing hormone in a pharmaceutically effective amount over a period of approximately five days, by means of a single injection, whereby multiple follicular growth may be induced in cattle.

14. A method for inducing multiple follicular growth in a female mammal comprising the step of injecting into the female the pharamceutical preparation of claim 1 prior to estrus.

15. The method of claim 14 wherein the female mammal is a cow and the injection is given approximately five days before estrus.

16. A method for inducing multiple follicular growth in a female mammal comprising the step of injecting into the female the pharmaceutical preparation of claim 8 prior to estrus.

17. The method of claim 16 wherein the female mammal is a cow and the injection is given approximately five days before estrus.

* * * * *